United States Patent
Hauger et al.

(10) Patent No.: US 8,230,866 B2
(45) Date of Patent: Jul. 31, 2012

(54) SYSTEMS AND METHODS FOR TREATING GLAUCOMA AND SYSTEMS AND METHODS FOR IMAGING A PORTION OF AN EYE

(75) Inventors: Christoph Hauger, Aalen (DE); Peter Andrews, Oberkocken (DE); Werner Nahm, Buehlertal (DE); Ralf Kuschnereit, Oberkochen (DE); Martin Hacker, Jena (DE); Gabor Scharioth, Recklinghausen (DE)

(73) Assignee: Carl Zeiss Meditec AG, Jena (DE)

( * ) Notice: Subject to any disclaimer, the term of this patent is extended or adjusted under 35 U.S.C. 154(b) by 354 days.

(21) Appl. No.: 12/000,477

(22) Filed: Dec. 13, 2007

(65) Prior Publication Data

US 2009/0157062 A1 Jun. 18, 2009

(51) Int. Cl.
*A61B 19/00* (2006.01)
(52) U.S. Cl. ................. 128/898; 606/4; 606/6
(58) Field of Classification Search .......... 606/4–6; 128/898
See application file for complete search history.

(56) References Cited

U.S. PATENT DOCUMENTS

| | | | | |
|---|---|---|---|---|
| 4,391,275 A * | 7/1983 | Fankhauser et al. | | 606/4 |
| 4,558,698 A * | 12/1985 | O'Dell | | 606/6 |
| 5,591,160 A * | 1/1997 | Reynard | | 606/15 |
| 5,865,831 A * | 2/1999 | Cozean et al. | | 606/6 |
| 6,220,247 B1 * | 4/2001 | Maldonado Bas | | 128/898 |
| 6,293,674 B1 * | 9/2001 | Huang et al. | | 351/221 |
| 2003/0097151 A1 * | 5/2003 | Smedley et al. | | 607/2 |
| 2004/0102729 A1 * | 5/2004 | Haffner et al. | | 604/8 |
| 2004/0109231 A1 | 6/2004 | Haisch et al. | | |
| 2006/0032507 A1 * | 2/2006 | Tu | | 128/898 |
| 2006/0106370 A1 * | 5/2006 | Baerveldt et al. | | 606/4 |
| 2006/0187462 A1 * | 8/2006 | Srinivasan et al. | | 356/479 |
| 2006/0206102 A1 * | 9/2006 | Shimmick | | 606/4 |

FOREIGN PATENT DOCUMENTS

| | | |
|---|---|---|
| EP | 0 697 611 A2 | 2/1996 |
| EP | 0697 611 B9 | 9/2002 |
| EP | 1 231 496 B1 | 12/2004 |
| WO | WO 2008/034609 | 3/2008 |

* cited by examiner

*Primary Examiner* — Ahmed Farah
(74) *Attorney, Agent, or Firm* — Kilpatrick Townsend & Stockton LLP (57) ABSTRACT

Systems and methods are described for imaging an eye portion or for treating glaucoma in an eye of a patient. In a first step an optical microscopic image of a portion of the eye is acquired. In the optical microscopic image a distinguishable anatomical structure is identified to predict a location of a volume portion to be imaged three-dimensionally. Three-dimensional imaging of the located volume portion is performed by acquiring an optical coherence tomography image of the located volume portion. The volume portion is treated by either directing a laser beam to the volume portion or inserting an implant based on the OCT-image.

27 Claims, 11 Drawing Sheets

SYSTEMS AND METHODS FOR TREATING GLAUCOMA AND SYSTEMS AND METHODS FOR IMAGING A PORTION OF AN EYE

BACKGROUND

1. Field of the Disclosure

The present invention relates to systems and methods for treating glaucoma in an eye of a patient. In particular, the present invention relates to systems and methods for treating glaucoma in an eye of a patient using a laser beam, systems and methods for treating glaucoma by inserting implants to an eye of a patient, and methods and systems for three dimensionally imaging a portion of an eye.

2. Background Information

Glaucoma is a severe disease of the eye, where the optic nerve is impaired. Glaucoma may lead to vision loss. One of the major risk factors for developing glaucoma is the intraocular pressure. Increased intraocular pressure can be treated by applying drugs. In cases where applying medication does not result in the desired decrease of intraocular pressure, surgery is another therapy. In such cases both laser surgery and conventional surgery are performed.

In many cases an increased intraocular pressure is due to an impaired balance between the production of aqueous humor in the ciliary body of the posterior chamber of the eye and the drainage of the aqueous humor within the anterior chamber of the eye through the trabecular meshwork and Schlemm's canal. Thus, many surgery strategies are directed to either modifying, that means in particular to decreasing, the production rate of aqueous humor or by modifying, that means in particular by increasing, the drainage rate of the aqueous humor from the anterior chamber. The production rate of aqueous humor is affected by treating the ciliary body in the posterior chamber of the eye. The drainage rate of the aqueous humor from the anterior chamber is affected by modifying structures in the trabecular meshwork, by introducing implants or tube shunts providing conduits from the posterior chamber to the anterior chamber or from the anterior chamber to the sclera or by manipulating Schlemm's canal.

Although considerably successes have been achieved during recent years, the accuracy with which surgical interventions can be performed is often not high enough. Thus, there is a need to provide improved methods for treating glaucoma in an eye of a patient.

SUMMARY

It is an object of the present disclosure to describe improved methods and systems for treating glaucoma in an eye of a patient by treating the eye by a laser beam or by inserting an implant into the eye.

It is a further object of the present disclosure to describe methods and systems for three dimensionally imaging of a portion of an eye.

According to an exemplary embodiment, a method for treating glaucoma of an eye of a patient is provided, wherein the method comprises locating a volume portion of the eye, acquiring a first OCT-image of merely the located volume portion of the eye by performing a first interferometric measurement, and then treating the volume portion by directing a laser beam to the volume portion to modify material in the volume portion of the eye based on the first OCT-image. Therein, the locating the volume portion is performed by acquiring an optical microscopic image of at least a part of the eye, identifying a distinguishable anatomical structure in the acquired optical microscopic image, and predicting a location of the volume portion based on the identified anatomical structure. In particular, the distinguishable anatomical structure identified in the acquired optical microscopic image may be located outside the volume portion of which the first OCT-image is acquired. Here, the optical microscopic image primarily serves as an auxiliary image in order to image the part of the eye and distinguish anatomical structures of the eye. By then using anatomical knowledge a location of the volume portion to be imaged three-dimensionally by optical coherence tomography (OCT) can be predicted. A scanning path can then be designed to scan a measuring beam across an area in order to acquire three-dimensional optical coherence tomography data of the located volume portion. These OCT-data form the first OCT-image. In particular, the optical path can be designed such that the volume portion is imaged three-dimensionally by OCT with a desired accuracy. The three-dimensional first OCT-image of the volume portion is then used to control a laser beam in order to direct the laser beam to the volume portion to modify the volume portion of the eye. Modifying of the volume portion of the eye may comprise photo-coagulation, applying burns, producing conduits, locally heating, and the like.

In OCT a beam comprising a broad range of wavelengths is split into a measurement beam and a reference beam. The measurement beam is directed to a sample to be measured, whereas the reference beam traverses a reference path. The measurement beam having interacted with the sample is interferometrically superimposed with the reference beam and detected. Due to the low coherence length an interference pattern only arises, if the two beams traversed two optical paths that differ less than the coherence length of the beams.

According to an exemplary embodiment, a method is provided wherein a second OCT-image of the volume portion of the eye is acquired by performing a second interferometric measurement and the volume portion is further treated by the laser beam based on at least one of the first and the second OCT images. Thereby, a change due to the treating the volume portion by the laser beam can be observed and measured and based on the measured change a further treating the volume portion can be performed. The treating may also be stopped when a desired result is already achieved.

According to an exemplary embodiment, the treating the volume portion by directing the laser beam to the volume portion comprises adjusting at least one of a) a laser output energy, b) a positioning of the laser beam and c) a spot size of the laser beam. This adjusting is based on at least one of the first OCT-image, the second OCT-image, and a difference between the first and the second OCT-images. Thus, the effect of a treating the volume portion by the laser beam in a previous step is taken into account to control the laser beam with respect to plural parameters to optimally adapt the laser beam for a treating in a next step of the surgery.

According to an exemplary embodiment, the acquiring at least one of the first and the second OCT-images comprises lateral scanning a measurement beam across the volume portion according to a scanning path and detecting light intensities emanating from scanned parts of the volume portion, wherein a geometry of the scanning path is based on the acquired optical microscopic image. Thus, before the first OCT-image is acquired, an optimal scan path for acquiring it may be designed based on the acquired optical microscopic image, and in particular based on an analysis of the acquired optical microscopic image. Thus, the scanning path for acquiring the OCT-image can be optimally adapted to the volume portion to be imaged three-dimensionally and to the desired accuracy.

According to an exemplary embodiment, the locating the volume portion comprises locating a volume portion in a cornea extending from an anterior chamber to the sclera close to an anterior chamber irido-corneal angle opening and close to a trabecular meshwork and wherein the treating comprises directing the laser beam to the located volume portion to modify material of the located volume portion.

According to an exemplary embodiment, the method further comprises analyzing at least one of the first and the second OCT-images to determine whether material is in the located volume portion in the cornea extending from the anterior chamber to the sclera as been modified providing a fluid conduit connecting the anterior chamber to the sclera through the cornea, wherein the treating is stopped when the fluid conduit is formed.

According to an exemplary embodiment, the locating the volume portion comprises locating a trabecular meshwork and the treating comprises modifying at least a part of the trabecular meshwork by the laser beam.

According to an exemplary embodiment, the method further comprises identifying in at least one of the first and the second OCT-images a Schlemm's canal, wherein the modifying of the at least part of the trabecular meshwork comprises preventing modifying Schlemm's canal.

According to an exemplary embodiment, the locating the volume portion comprises locating an iris and the treating comprises modifying the iris by the laser beam to provide a fluid conduit connecting an anterior chamber to a posterior chamber of the eye through the iris.

According to an exemplary embodiment, the locating the volume portion comprises locating a ciliary body adjacent to a posterior chamber of the eye an the treating comprises modifying the ciliary body by the laser beam.

According to an exemplary embodiment, a method for treating glaucoma in an eye of a patient is provided, comprising locating a volume portion of the eye, acquiring a first OCT-image of the located volume portion of the eye by performing a first interferometric measurement and then treating the volume portion by inserting an implant at the volume portion based on the first OCT-image. Thus, a method for treating glaucoma is provided, wherein a manual surgery is performed utilizing three-dimensional data of the volume portion which data are acquired by performing optical coherence tomography. Thus, the surgeon has three-dimensional data of the volume portion at hand, to navigate to a particular structure to be manipulated. In particular, an implant is inserted by the surgeon at a particular location of the volume portion of the eye. As in a method according to other embodiments, the locating the volume portion of the eye comprises acquiring an optical microscopic image of at least a part of the eye, identifying a distinguishable anatomical structure in the acquired optical microscopic image, and predicting a location of the volume portion based on the identified anatomical structure. Thus, it is avoided to acquire OCT-data of regions of the eye that are not required to be imaged to perform the current surgery. Thus, damage to these portions is avoided and an acquisition time to acquire the OCT-image may be shortened. Also, an accuracy of the OCT-image can be adapted, to optimally image in three dimensions that volume portion of the eye most important for performing the surgery.

According to an exemplary embodiment, the method further comprises acquiring a second OCT-image of the volume portion of the eye by performing a second interferometric measurement, and further treating the volume portion based on at least one of the first and the second OCT-images. Thus, a surgeon can accurately monitor a course of the surgery and based on the current stage of the surgery he or she can continue treating the volume portion.

According to an exemplar embodiment, the locating the volume portion comprises locating a Schlemm's canal and the treating comprises inserting a fiber into at least a part of the Schlemm's canal.

According to an exemplary embodiment, the method further comprises analyzing at least one of the first OCT-image, the second OCT-image, and the optical microscopy image to determine an amount of dilatation of the Schlemm's canal due to the inserted fiber.

According to an exemplary embodiment, the method further comprises adjusting at least one of a positioning and a length of the fiber such that an amount of dilatation of the Schlemm's canal deviates less than a predetermined threshold from a predetermined amount of dilatation.

According to an exemplary embodiment, a method is provided, wherein the locating the volume portion comprises locating a Schlemm's canal and locating an anterior chamber and wherein the treating comprises inserting a tube shunt into a portion of the eye such that the tube shunt provides a fluid conduit from the anterior chamber to the Schlemm's canal.

According to an exemplary embodiment, the locating the volume portion comprises locating a sclera and locating an anterior chamber and wherein the treating comprises inserting a tube shunt into a portion of the eye such that the tube shunt provides a fluid conduit from the anterior chamber to the sclera.

According to an exemplary embodiment, a method for imaging a volume portion of an eye of a patient is provided, wherein the method comprises acquiring an optical microscopic image of a part of the eye, identifying a distinguishable anatomical structure in the acquired optical microscopic image, predicting a location of the volume portion based on the identified anatomical structure, and acquiring an OCT-image of merely the volume portion of the eye by performing an interferometric measurement based on the predicted location. The optical microscopic image of the part of the eye serves as an auxiliary image to visualize and distinguish anatomical structures in the eye. By using anatomical knowledge, in particular by analyzing the acquired optical microscopic image by performing image processing using a library of images of anatomical structures, a location of the volume portion comprising structures to be imaged three dimensionally can be predicted. The predicted location can then be used to design an optimally designed scanning path for acquiring an OCT-image.

According to an exemplary embodiment, the volume portion is located outside the identified anatomical structure.

According to an exemplary embodiment, the volume portion comprises an anatomical structure different from the distinguishable anatomical structure identified in the acquired optical microscopic image.

According to an exemplary embodiment, the acquiring the OCT-image comprises lateral scanning a measurement beam across the volume portion according to a scanning path and detecting light intensities emanating from scanned parts of the volume portion, wherein a geometry of the scanning path is based on the acquired optical microscopic image.

According to an exemplary embodiment, the lateral scanning is performed using a scanning apparatus having a maximal scanning range, wherein the lateral scanning across the volume portion comprises less than 80%, in particular less than 50%, in particular less than 20%, of the maximal scanning range.

According to an exemplary embodiment, the method further comprises analyzing the acquired OCT-image to determine at least one of a volume, a position relative to anatomical structures, distinguishable in at least one of the OCT-image and the optical microscopic image, and a three-dimensional extension of a predetermined distinguishable anatomical structure in the volume portion, wherein the predetermined anatomical structure is in particular at least a part of a Schlemm's canal.

According to an exemplary embodiment, a system for imaging a volume portion of an eye is provided, wherein the system comprises an optical microscopic apparatus and an OCT-imaging apparatus. Hereby, the optical microscopic apparatus comprises a light source for illuminating a part of the eye, an imaging optics for imaging the illuminated part of the eye to an image plane of the imaging optics, a spatially resolving detector arranged in the image plane for acquiring an optical microscopic image of the part of the eye, and an image processing system for analyzing the acquired optical microscopic image, wherein the analyzing comprises identifying at least one distinguishable anatomical structure in the optical microscopic image based on the optical microscopic image and at least one reference image comprised in a data storage to predict a location of the volume portion. Hereby, the OCT-imaging apparatus comprises a beam source for generating a measurement beam and a reference beam, an OCT-controlling system for directing the measurement beam merely to the volume portion using the predicted location of the volume portion, an interferometer for interferometrically superimposing the reference beam with a light beam emanating from the volume portion, a detector for detecting the interferometrically superimposed light beams, and a data processor system for computing a representation of the volume portion based on the detected superimposed light beams.

According to an exemplary embodiment, the system further comprises a display device for displaying at least one of the optical microscopic image and the representation of the volume portion.

According to an exemplary embodiment, a system for treating glaucoma in an eye of a patient is provided comprising the system for imaging a volume portion of the eye and a laser treatment apparatus. The laser treatment apparatus comprises a laser source for generating a laser beam, laser shaping and directing optics for shaping the laser beam and directing the shaped laser beam to the volume portion, and a laser controlling system for controlling at least one of an output energy of the laser beam, a positioning of the laser beam, and a spot size of the laser beam based on at least one OCT-image acquired by the OCT-imaging apparatus.

BRIEF DESCRIPTION OF THE DRAWINGS

Exemplary embodiments will now be described with reference to the accompanying drawings, wherein same or similar reference numerals denote same or similar elements.

DETAILED DESCRIPTION OF EXEMPLARY EMBODIMENTS

Figure 1:
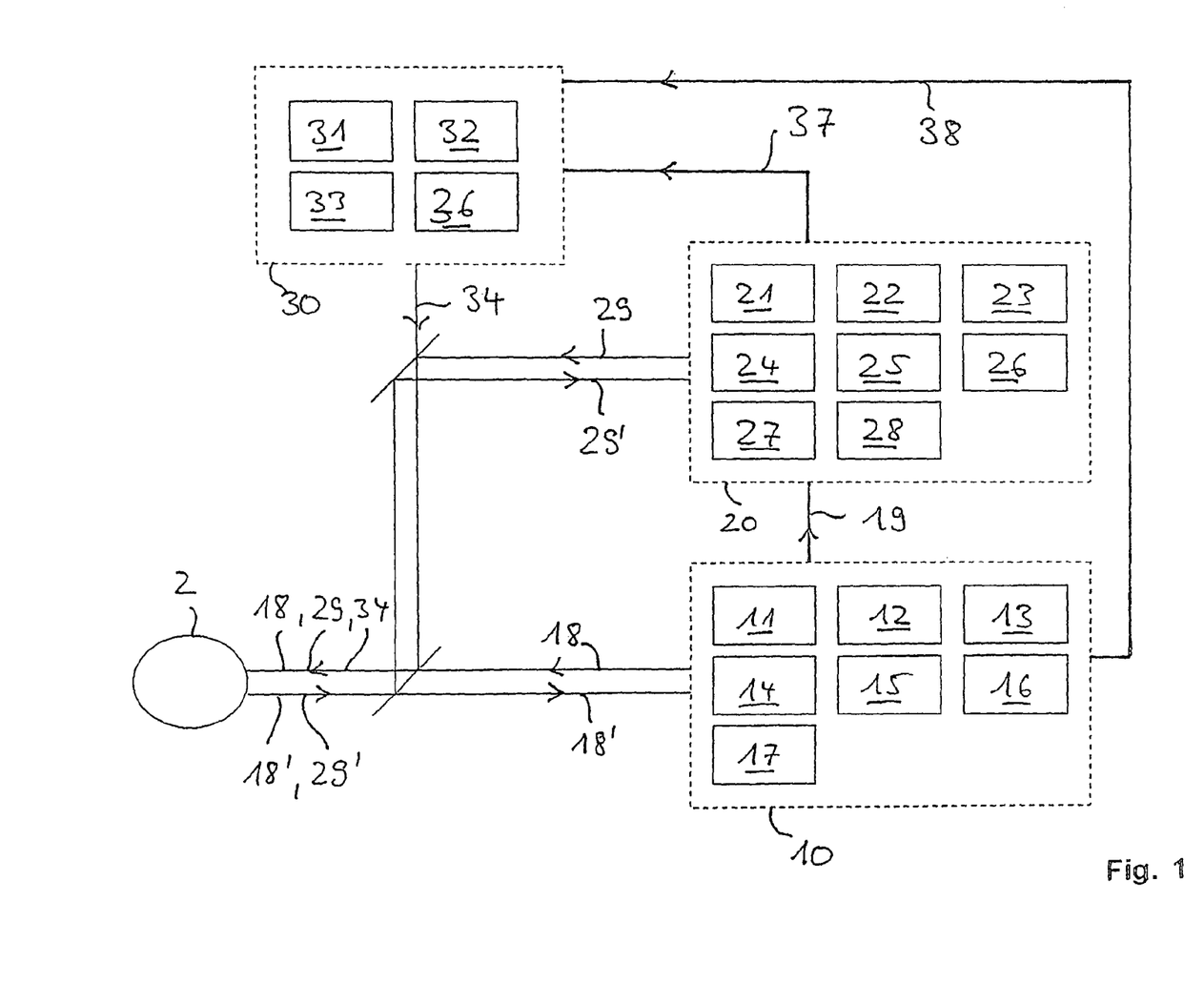
FIG. 1 schematically illustrates a system of an exemplary embodiment according to the present disclosure for performing methods according to the present disclosure.

FIG. 1 schematically illustrates a system 1 of an embodiment according to the present invention for performing embodiments of methods according to the present invention. The system 1 is adapted to treat glaucoma in an eye 2 of a patient. The system 1 comprises an optical microscopic apparatus 10, an optical coherence tomography (OCT) apparatus 20, and a laser treatment apparatus 30.

Information regarding the general construction and details about optical elements of such a system are described in the European patent application EP 0 697 611 A2 the full content of which is incorporated by reference into this application. However, the inventive system 1 additionally comprises elements and devices for controlling the system 1 as set forth below.

The optical microscopic apparatus 10 comprises a light source 11 for producing a light beam 18 for illumination of at least a part of the eye 2 for which the light source also comprises illumination optics. A light beam 18' emanates from the illuminated part of the eye 2 which is used to image the part of the eye by the optical microscopic apparatus 10. For this the optical microscopic apparatus 10 further comprises imaging optics 12 to image the part of the eye disposed in an object plane of the imaging optics 12 to an image plane of the optical microscopic apparatus. The part of the eye 2 can further be imaged from the image plane to a CCD detector 13 comprising camera optics. Thereby, an optical microscopic image of the part of the eye 2 can be acquired. Also, an observer or surgeon can use the oculars 14 to observe the imaged part of the eye 2. In addition, the optical microscopic image detected by the CCD 13 can be displayed on the monitor 15 in particular with additional information regarding imaging conditions and the like.

Furthermore, the optical microscopic apparatus 10 is equipped with an imaging processing and storage device 16 to process and store optical microscopic images. For this, the optical microscopic apparatus 10 further comprises a library of images of anatomical structures (reference data) that are used to identify structures in the acquired optical microscopic images. Depending on the particular application at least one reference image of an anatomical structure, such as an iris or Schlemm's canal, is comprised in the library of images. The processing for identification of anatomical structures within the optical microscopic images may comprise calculating correlation functions between the image or images of anatomical structures stored within the library 17 and the optical microscopic image or images acquired from the part of the eye 2. Based on a location of a matched anatomical structure within the acquired optical microscopic image a location of a volume portion comprising a structure to be treated can be predicted. For selecting such a structure to be treated the optical microscopic apparatus 10 further comprises an input device 17, such as a keyboard or voice input. The prediction of the location of the volume portion also uses an anatomical knowledge base comprised in the imaging and storage device 16 where information representing a relative positioning and orientation of anatomical structures is stored.

The optical microscopic apparatus 10 is connected to the OCT apparatus 20 by a connection line 19. Via this connection line 19 data relating to location information of the volume portion can be transmitted from the optical microscopic apparatus 10 to the OCT apparatus 20.

The OCT apparatus 20 comprises a beam source 21 for generating a measurement beam 29. The measurement beam 29 is shaped by beam shaping optics 22 which may comprise lenses, mirrors and/or diffractive optical elements and the measurement beam 29 is directed to a portion of the eye 2. Further, the OCT apparatus 20 comprises a scanning apparatus 23 for scanning the measurement beam 29 across an area of the eye 2 in order to acquire an OCT-image of a volume portion of the eye 2. The scanning apparatus 23 is adapted to maximally scan across a particular area of an object to be imaged, i.e. scanning apparatus 23 has a maximal scanning range. For controlling the positioning of the OCT measurement beam 29 during scanning the volume portion of the eye 2 transformation operations are established to convert positional information in the optical electron microscopic images to positioning information of the scanning apparatus 23 of the OCT apparatus 20.

Light beam 29' emanating from the volume portion of the eye is interferometrically superimposed with a reference beam provided by the reference beam former 24 of the OCT apparatus 20. The reference beam former 24 is capable for adjustment of a reference beam path length. The detector 26 of the OCT apparatus 20 detects light intensities resulting from interfering light emanated from the volume portion of the eye 2 and light of the reference beam of the OCT apparatus 20.

The OCT apparatus 20 can be configured to be a time domain OCT apparatus (TD-OCT) or may be configured to be a frequency-domain apparatus (FD-OCT). TD-OCT differs from FD-OCT in the way depth scanning is performed to acquire depth information of a point of the volume portion.

In both kinds of OCT, TD-OCT and FD-OCT, a sample is illuminated with a broad band light source, that means a light source comprising light waves of a range of wavelengths. Thus, this kind of light exhibits a low coherence length. Two beams of this kind of light can only interfere, when their difference of optical path lengths traversed is less than the coherence length of the light source. In TD-OCT the optical path length traversed by the reference beam is changed in order to allow light reflected from different depths of the sample to interfere with the reference beam. In FD-OCT the optical path length traversed by the reference beam is substantially fixed. Instead, depth information of the sample is obtained by analyzing the interfered light with respect to the comprised wavelengths. For this, the FD-OCT apparatus typically comprises a spectrometer to split light reflected from the sample with respect to different wavelengths comprised therein, wherein the Fourier transform of the acquired spectrum gives the depth scan of the sample. FD-OCT can be configured in the form of Fourier domain-OCT or in the form of swept source-OCT. The methods according to the present invention can be performed with any such kind of OCT apparatus.

For computing the three-dimensional volume data from the intensities detected by the detector 26, the OCT apparatus 20 comprises an image processing device 27. OCT-images representing the volume portion computed by the image processing device 27 are displayed on the monitor 28.

The system 1 is further adapted to track a location of an object detail imaged in one OCT-image to a location of the same object detail imaged in a second OCT-image. Herein, using computation, the two three-dimensional images are compared to each other, such as by cross correlation techniques, in order to determine a displacement vector describing the change of the location of the object detail. According to the tracked change of the location of the object detail the system then controls the scanning apparatus 23 of the OCT apparatus 20 in order to keep the object in the scanning range, i.e. in the field of view of system 1. Thus, even if an object detail moves during examination of treating it can always be imaged using the OCT-apparatus 20.

The system 1 further comprises a laser treatment apparatus 30 for treating a volume portion of the eye 2. The laser treatment apparatus 30 comprises a laser source 31 for generating a laser beam 34. Laser beam shaping is performed by the shaping optics 32 and positioning of the beam is performed by the positioning device 33. Laser beam 34 is directed to a volume portion of the eye 2. The energy output of the laser beam 34, defocusing, and the spot size of the laser beam 34 at the volume portion of the eye 2 is controlled by the laser controller 36. For this, the laser controller 36 is connected to the OCT apparatus 20 and to the optical microscopic apparatus 10 via connection lines 37, respectively 38. For controlling the positioning of the laser beam focusing spot 34' in the volume portion of the eye 2 transformation operations are established to convert positional information in the OCT-images and the optical microscopic images to positioning information of the laser beam.

Figure 2:
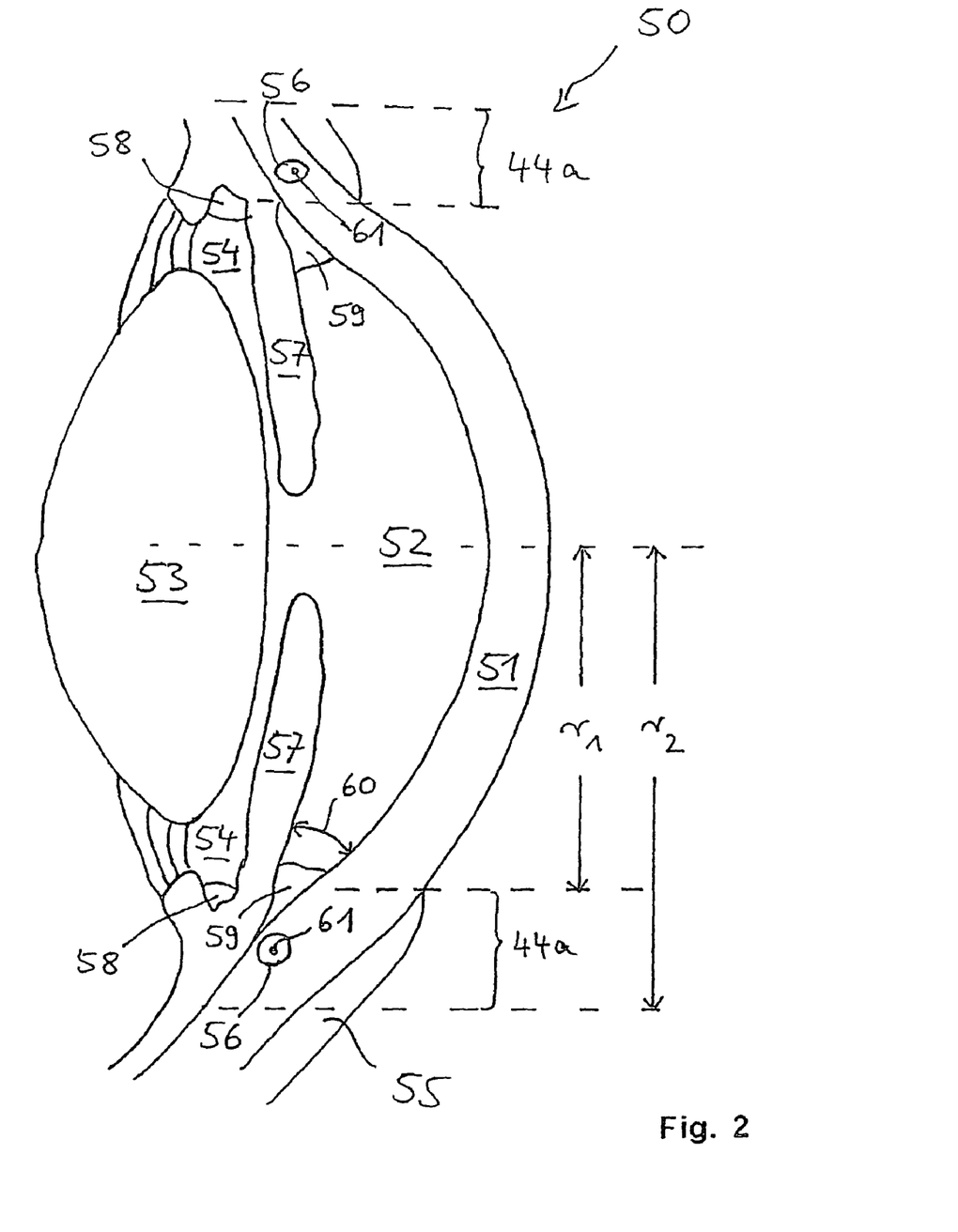
FIG. 2 illustrates a method for imaging and treating a volume portion of an eye according two exemplary embodiments of the present disclosure.
Figure 3:
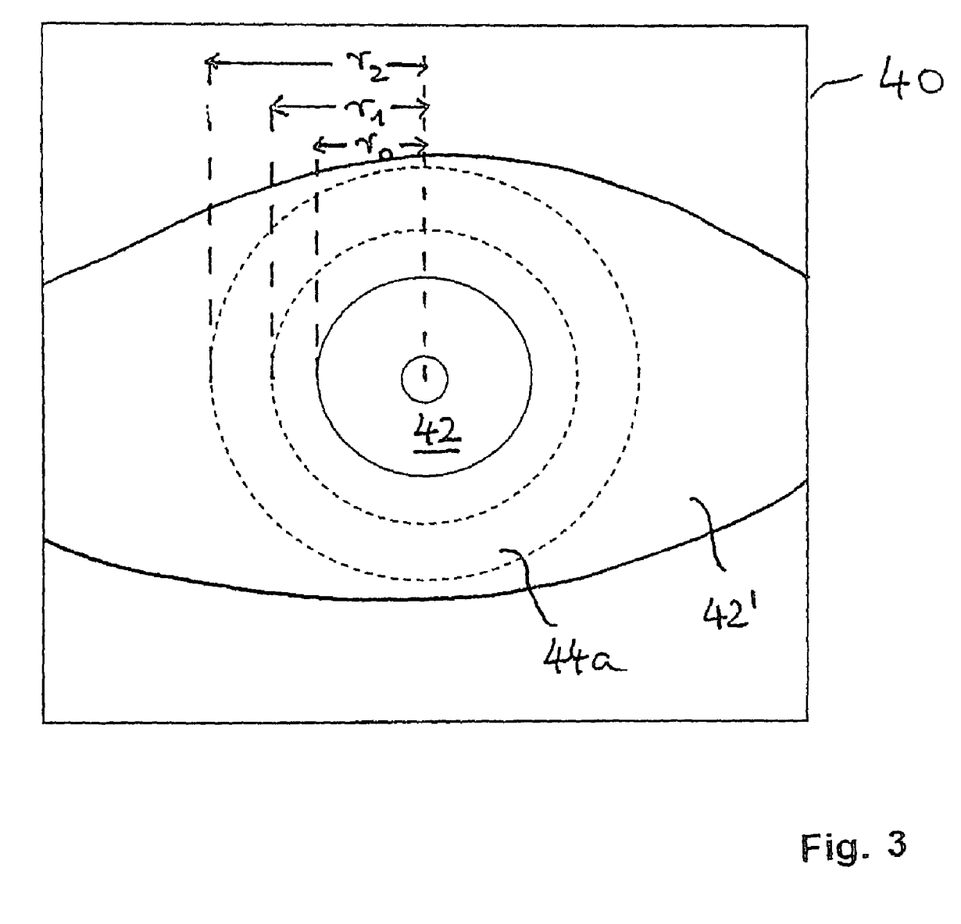
FIG. 3 schematically illustrates an optical microscopic image acquired during a step according to exemplary embodiments of a method according to the present disclosure.

FIGS. 2, 3, 4a to 4d, and 5 schematically illustrate an embodiment of a method according to the present invention. An anterior eye portion 50 is schematically illustrated in FIG. 2 comprising a cornea 51, an anterior chamber 52 of the eye, a crystalline lens 53, a posterior chamber 54 of the eye, a sclera 55, a Schlemm's canal 56, an iris 57, a ciliary body 58, a trabecular meshwork 59, and an irido-corneal angle opening 60. In the particular treatment illustrated in FIGS. 2, 3, 4a to 4d, and 5 it is intended to introduce a fiber 61 into Schlemm's canal 56, in order to dilate Schlemm's canal 56 to increase a drainage rate of aqueous humor to lower the intra-ocular pressure. In a first step of performing this treatment an optical microscopic image 40 is acquired as illustrated in FIG. 3.

By analyzing the optical microscopic image 40 anatomical structures 42 and 42' are identified. In this case, the anatomical structure 42 is the iris and the anatomical structure 42' is the sclera of the eye. Based on the analysis of the optical microscopic image 40 and based on anatomical knowledge a volume portion 44a can be located supposedly comprising Schlemm's canal. In the example illustrated, the volume portion 44a is delimited by two cylinder surfaces having radiuses $r_1$ and $r_2$, wherein according to anatomical knowledge the radius $r_1$ is by an amount $r_0$ larger than the radius $r_{iris}$ of the iris 42 and the radius $r_2$ is larger than the radius $r_1$ by another amount known from anatomy that may depend on particular conditions of the patient such as age, sex of the like. Thus, both radiuses $r_1$ and $r_2$ can be computed upon analyzing the electron microscopic image 40, thereby defining the volume portion 44a.

Figure 5:
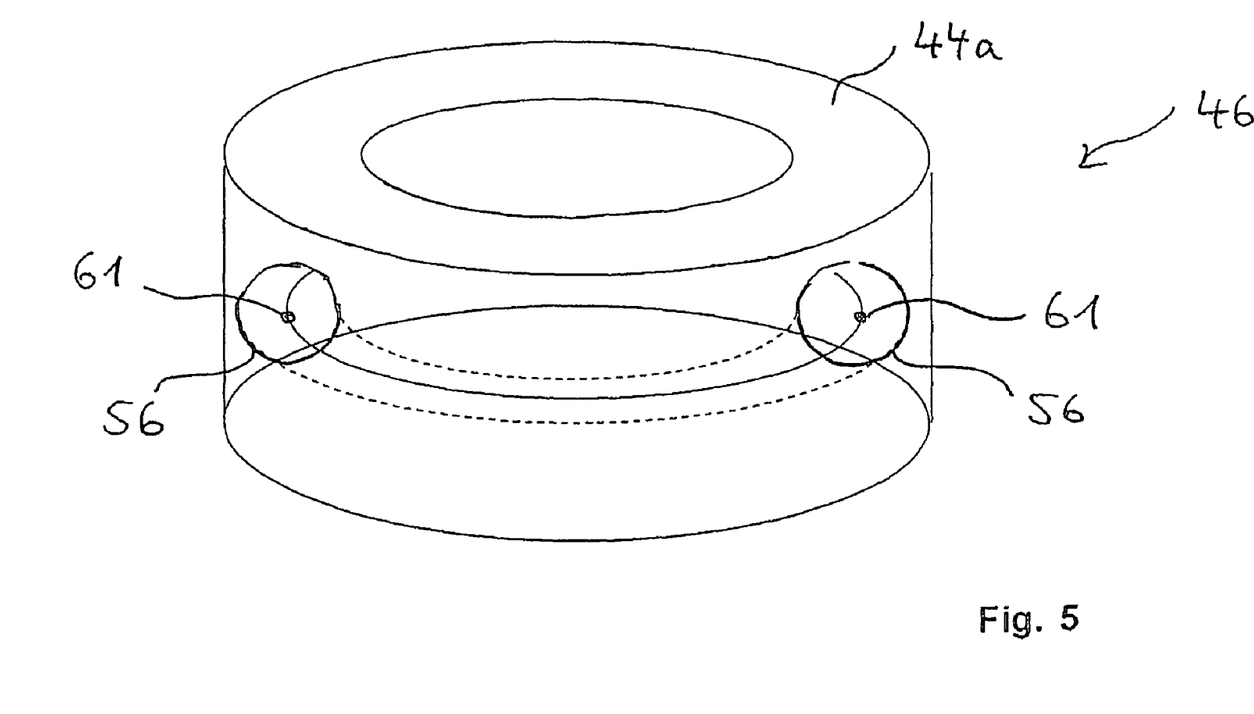
FIG. 5 schematically illustrates an OCT-image acquired in an exemplary embodiment of a method according to the present disclosure.

The location information of the volume portion 44a is transferred from the optical microscopic apparatus 10 to the OCT apparatus 20 via connection line 19, wherein necessary transformation operations are performed to convert coordinate values related to different coordinate systems. Based on the location information, the OCT apparatus 20 acquires an OCT-image 46 of the volume portion 44a of the eye as illustrated in FIG. 5. In the volume portion 44a the three-dimensional structure of the entire Schlemm's canal 56 is visualized. For a surgeon, it is thus possible to insert a fiber 61 into Schlemm's canal 56 using the OCT-image 46 of the volume portion 44a comprising the Schlemm's canal 56. One or more such OCT-images 46 may be analyzed to obtain information of the Schlemm's canal 56 regarding geometrical properties, such as to obtain a volume of the Schlemm's canal, a circumference of the Schlemm's canal and/or a cross section of the Schlemm's canal 56. After inserting the fiber 61 such kind of geometrical properties of the Schlemm's canal 56 may be re-measured in order to monitor a desired modification of the geometrical properties. In particular, it may be desirable to dilate the Schlemm's canal by the insertion of the fiber 61. Thus, using at least one OCT-image 46 the surgeon can manipulate a length, a positioning and the like of the fiber 61 in order to achieve a desired effect.

If an object detail moves between or during acquisition of OCT-images this can be tracked by the system 1. Illumination and imaging optics are controlled such that it is ensured the object detail always remains within the field of view of the OCT-apparatus and the optical microscopic apparatus. Thereby the surgeon is enabled to perform the required treatments on the object detain of the eye while monitoring the progress of the treatment.

Figure 4A:
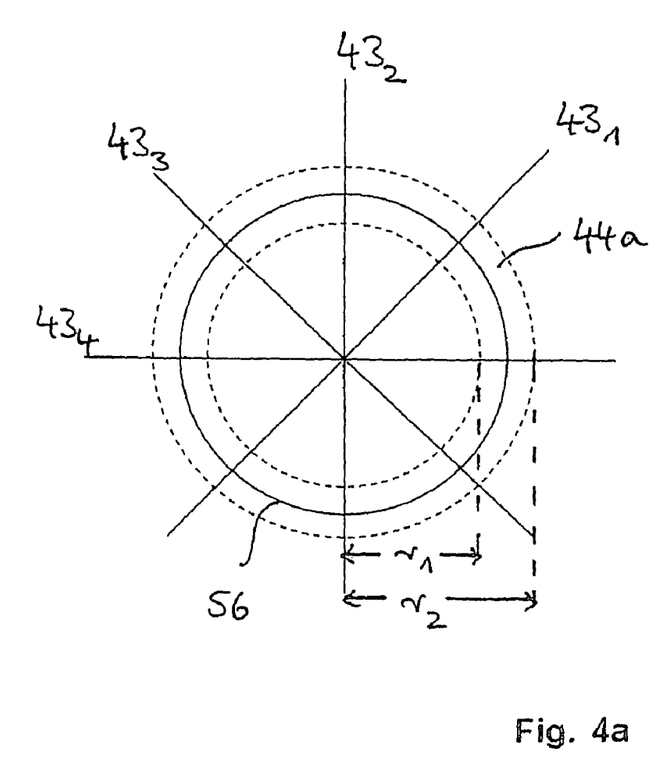
FIG. 4a, FIG. 4b, FIG. 4c, and FIG. 4d schematically illustrate scanning paths for acquiring OCT-images according to exemplary embodiments of the present disclosure.

FIGS. 4a, 4b, 4c and 4d illustrate scanning paths 43 used for acquiring an OCT-image 46 of the volume portion 44a illustrated in FIGS. 2, 3, and 5. The volume portion 44a supposedly comprises the Schlemm's canal 56. In FIG. 4a four scanning paths segments $43_1$, $43_2$, $43_3$, and $43_4$ are illustrated to intersect the Schlemm's canal 56 substantially at right angles at eight positions along the perimeter of the Schlemm's canal 56. These scanning path segments are traversed subsequently to provide a combined scan path 43.

Figure 4B:
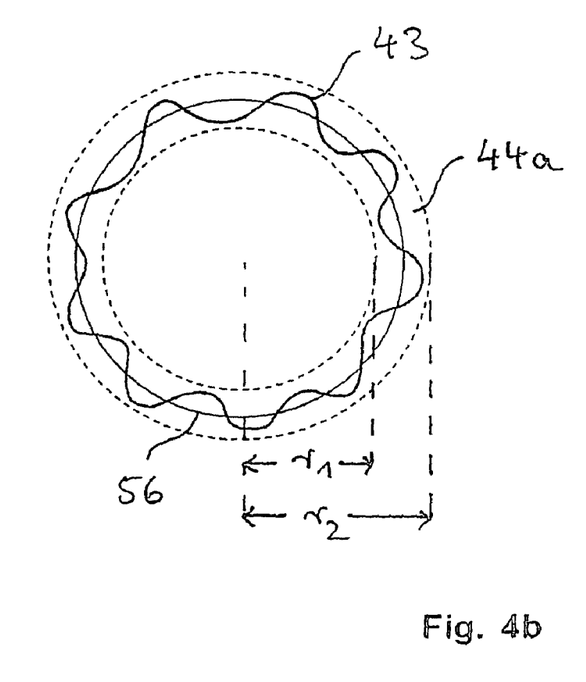

A further possibility of a geometry of a scanning path 43 is illustrated in FIG. 4b. Scanning path 43 is designed as a meander-shaped path crossing the Schlemm's canal 56 several times.

Figure 4C:
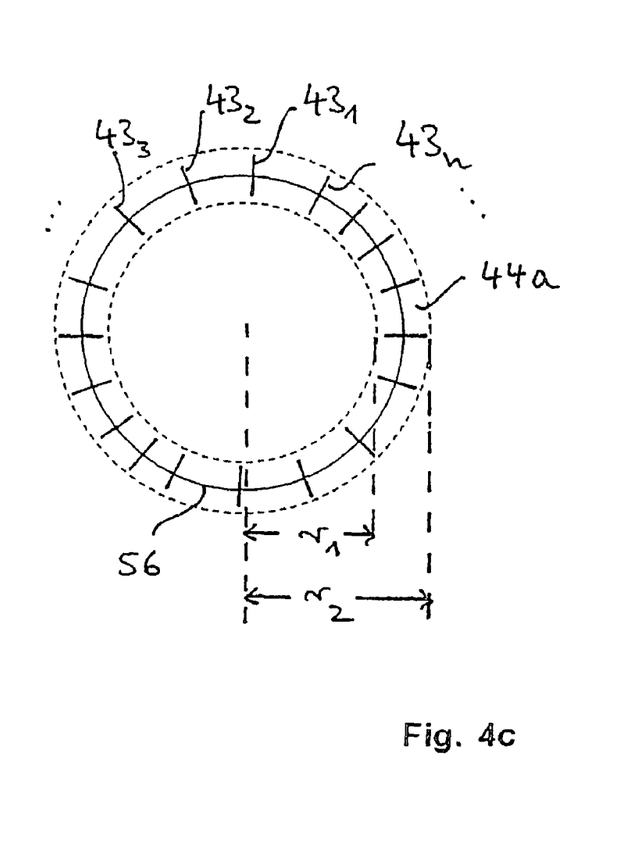

FIG. 4c illustrates a plurality of short radial scanning paths segments $43_1$, $43_2$, . . . , $43_n$ to scan the volume portion 44a comprising the Schlemm's canal 56.

Figure 4D:
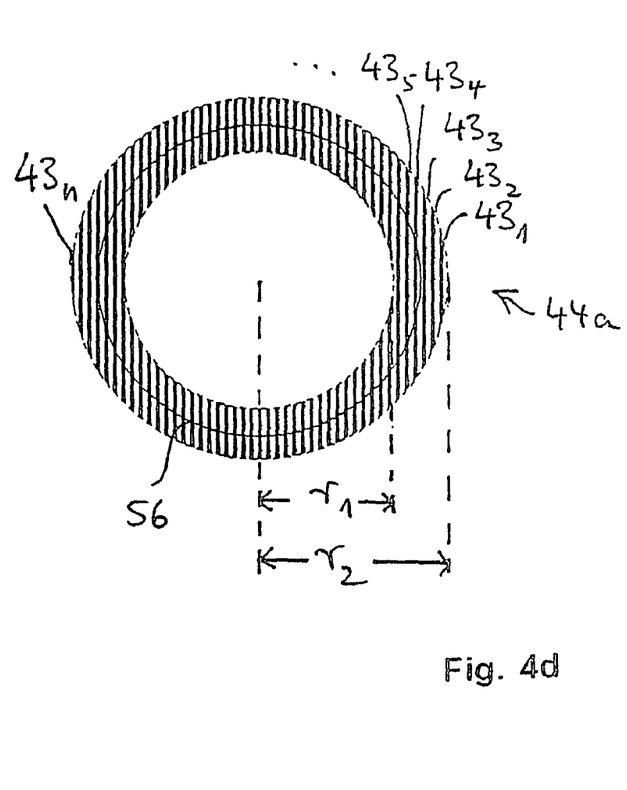

FIG. 4d illustrates scanning path segments $43_1$, $43_2$, $43_3$, . . . , $43_n$ comprising a plurality of straight lines parallel to each other which lie inside an outer circle with radius $r_2$ and outside an inner circle with radius $r_1$. The same radiuses are indicated in FIGS. 2 and 3. The scanning path illustrated in FIG. 4d illustrates a scanning path with highest lateral scanning accuracy.

Depending on needs for an application, one or more of the scanning paths 43 illustrated in FIGS. 4a, 4b, 4c and 4d can be combined to acquire an OCT-image or may be applied to subsequently acquire different OCT-images.

Figure 6:
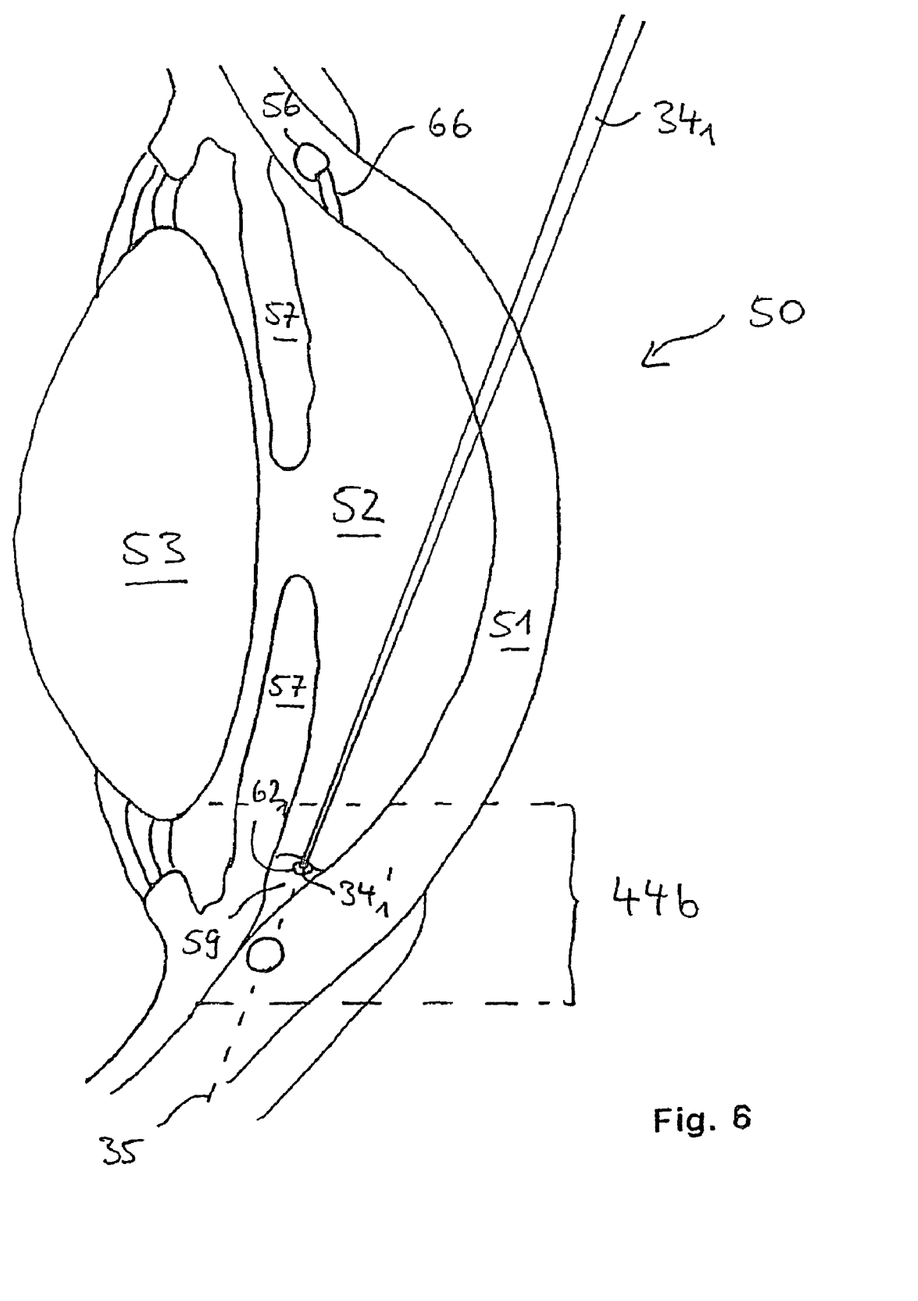
FIG. 6 schematically illustrates a method step in an exemplary embodiment of a method for treating glaucoma in an eye according to the present disclosure.
Figure 7A:
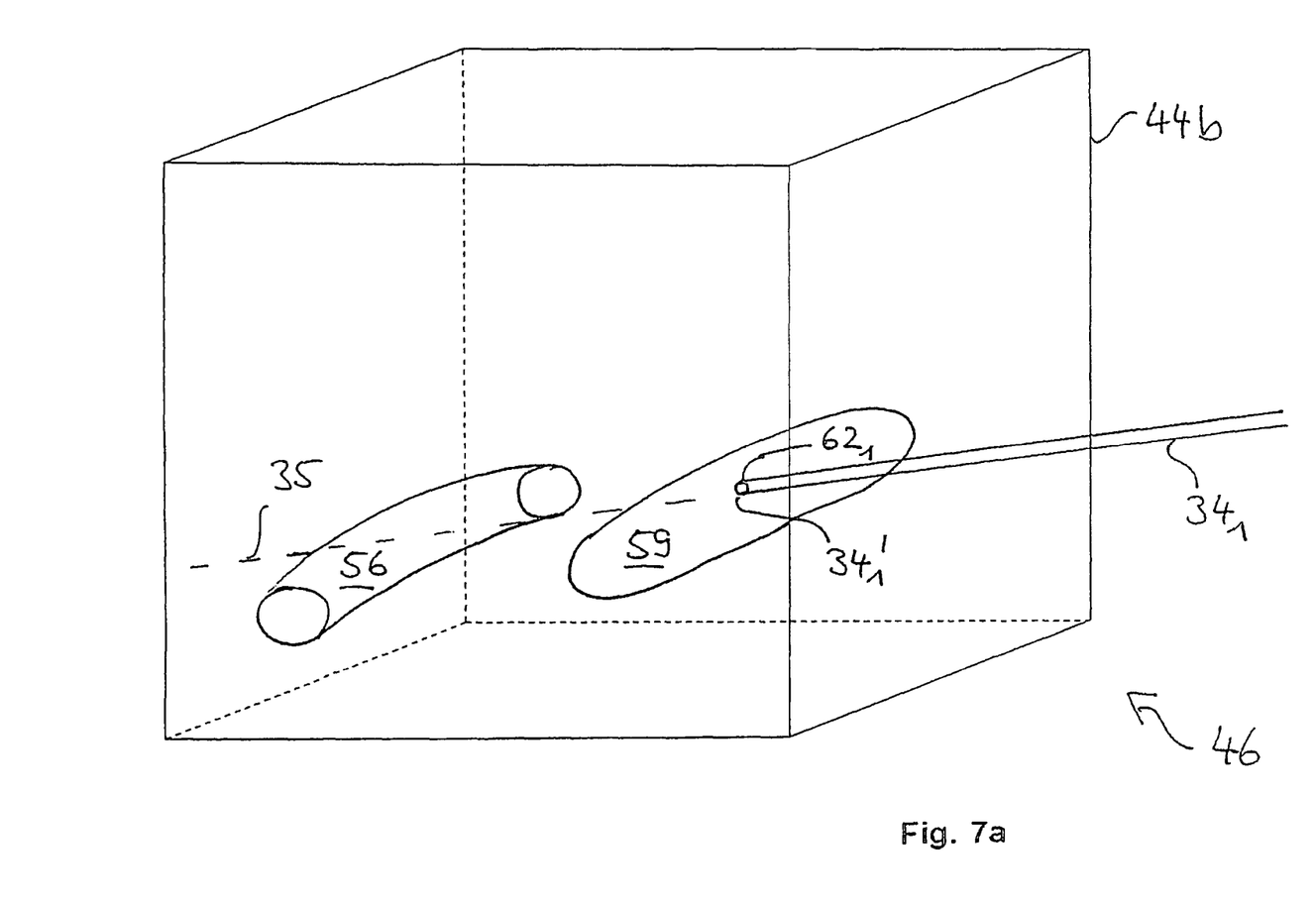
FIG. 7a and FIG. 7b schematically illustrate method steps in a method for treating glaucoma in an eye of a patient according to an exemplary embodiment of the present disclosure.
Figure 7B:
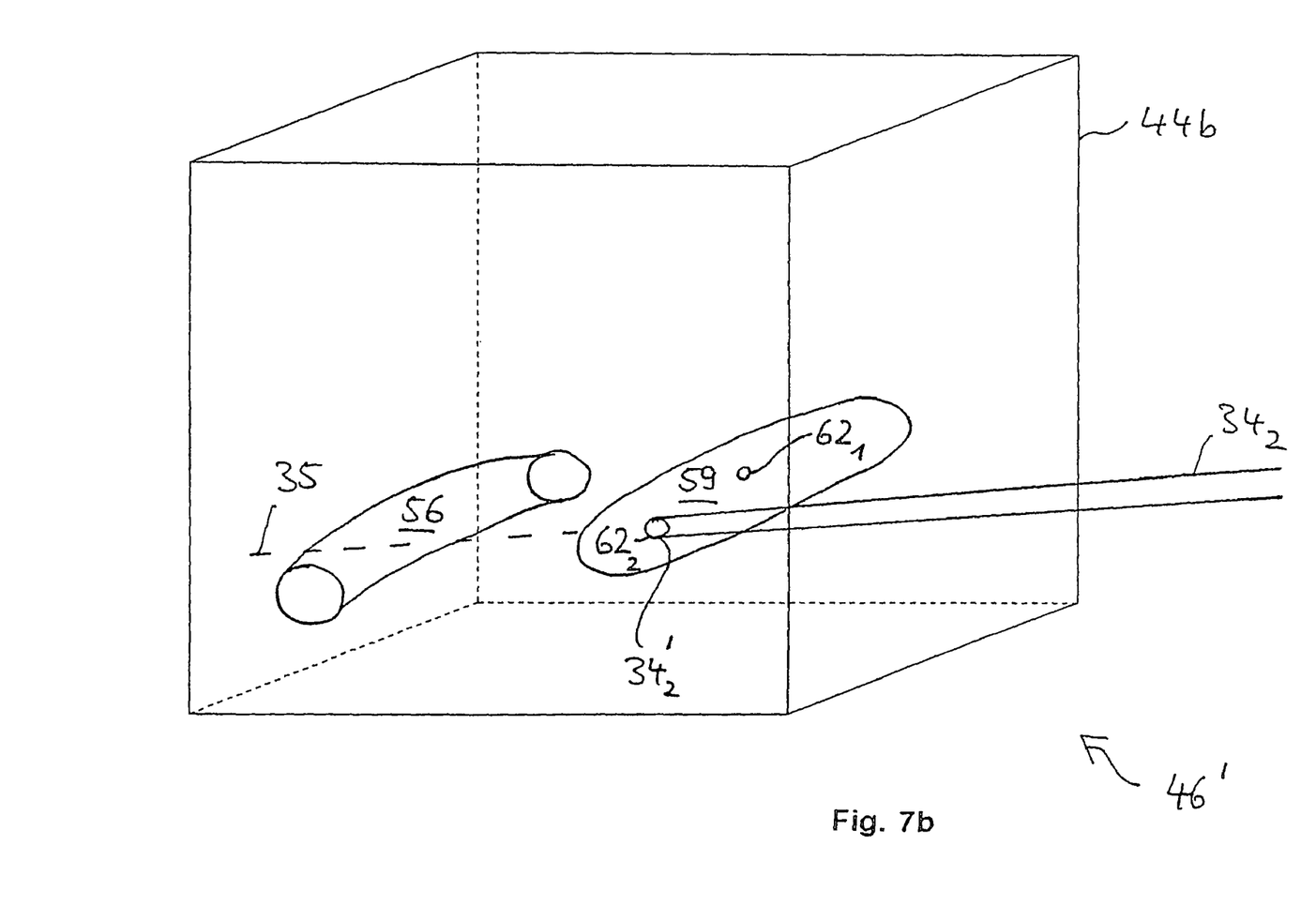

FIGS. 6, 7a, and 7b illustrate another method according to an embodiment of the present invention. In the illustrated example, it is intended to modify regions of the trabecular meshwork 59 in the anterior chamber 52 of the eye. In order to modify regions of the trabecular meshwork 59 a laser beam $34_1$ of the laser treatment apparatus 10 is initially directed to the trabecular meshwork 59 to be focused in a focusing point 3411 as illustrated in FIG. 6. In this cross sectional view of the anterior eye 50 also a volume portion 44b in a cross section is illustrated from which OCT-images 46 and 46' are acquired according to the inventive method. OCT-images 46 and 46' acquired from the volume portion 44b are illustrated in FIGS. 7a and 7b, respectively. The modifying the trabecular meshwork is aimed to apply small burns $62_1$, $62_2$ to several locations of the trabecular meshwork without impairing or damaging the Schlemm's canal 56. Because of the anatomical conditions, however, the Schlemm's canal 56 appears to be situated in line with the laser beam $34_1$ traversing in a direction 35, as illustrated in FIGS. 6, 7a and 7b. Therefore, there is a risk that the laser beam 34 may damage the Schlemm's canal 56, when the treating the trabecular meshwork 59 is performed too long or with too high laser output energy such that the laser beam $34_1$ traverses up to the Schlemm's canal 56. Thus, in particular for this kind of treatment of glaucoma it is necessary to three-dimensionally image a portion of the anterior eye 50 and control the laser beam 34 with respect to its positioning, focusing, and/or spot size based on the three-dimensional image 46, 46' to improve a success rate of the surgery. In the particular case illustrated the focusing point $34_1$' of the laser beam $34_1$ is moved to an adjacent focusing point $34_2$' before the Schlemm's canal is affected by the laser beam. The focusing point $34_2$' additionally has a larger spot size than the focusing point $34_1$' and the energy of the laser beam $34_2$ is transferred to a larger area of the trabecular meshwork 59. Thus, using the three dimensional images 46, 46' enables avoiding damage of the Schlemm's canal 56 during treatment of the trabecular meshwork 59.

In another region of the anterior eye 50 illustrated in FIG. 6 a tube shunt 66 is inserted connecting the Schlemm's canal with the anterior chamber 52 of the eye. Also this surgery was performed using OCT-images for monitoring and/or adjusting a proper positioning of the tube shunt 66.

Figure 8:
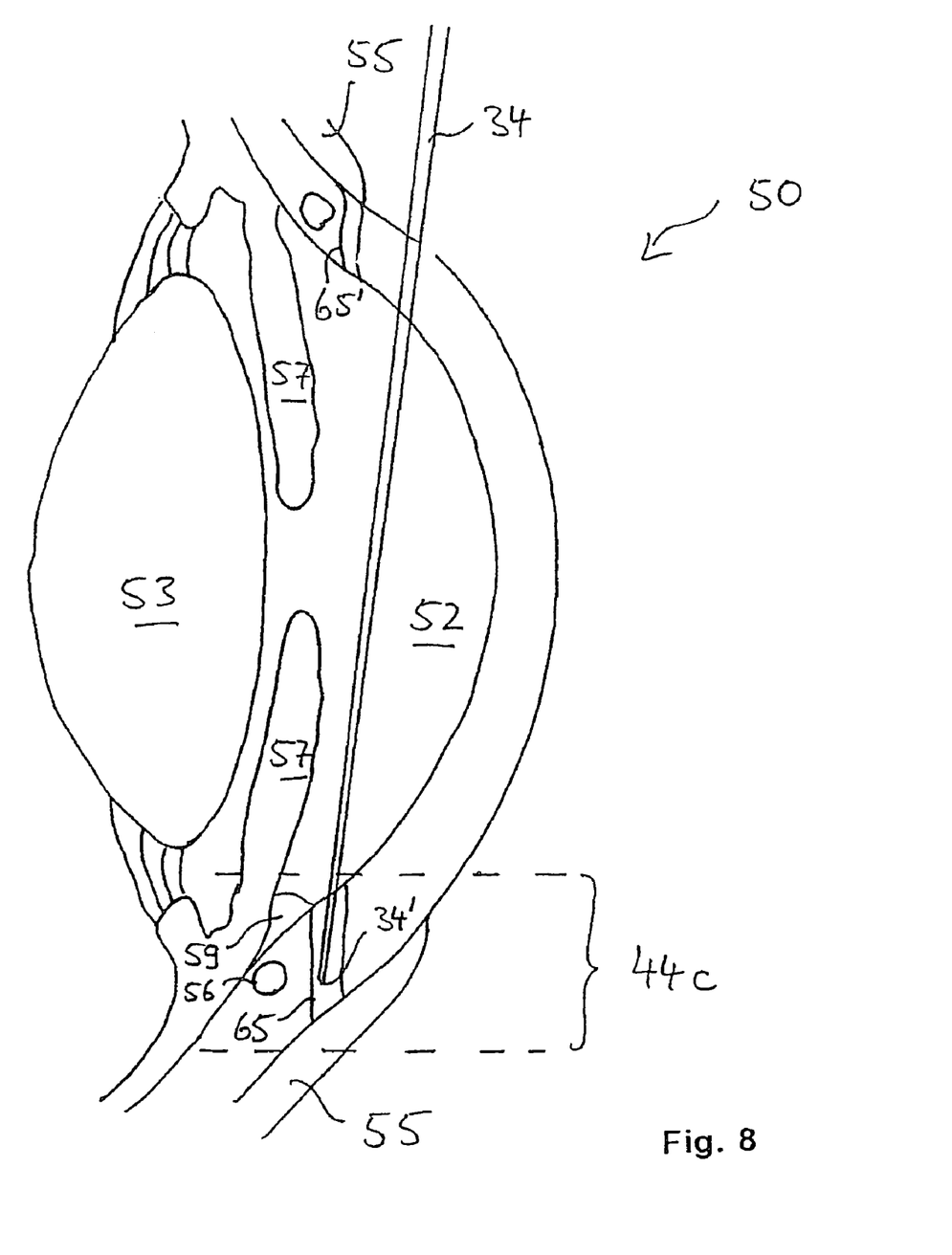
FIG. 8 schematically illustrates a method step in a method for treating glaucoma in an eye of a patient according to an exemplary embodiment of the present disclosure.

FIG. 8 illustrates an example of an embodiment according to the present invention. During this surgical treatment a fluid conduit 65 is to be formed from the anterior chamber 52 through the cornea 51 to the sclera 55 for increasing a drainage rate of aqueous humor. In order to form the conduit a laser beam 34 irradiated from the laser treatment apparatus 30 is directed to the cornea 51 and focused at a focusing point 34'. The cornea 51 irradiated by the laser beam is modified, for example photo ablated. To monitor a progress of the laser beam treatment an OCT-image is acquired from a volume portion 44c. This volume portion 44c has been determined based on an optical microscopic image acquired from the anterior eye portion in a previous method step. In the not illustrated OCT-image of the volume portion 44c the forming of the conduit from the anterior chamber 52 of the eye to the sclera can be monitored and the output energy of the laser beam 34, the positioning, and/or the spot size of the laser beam 34 can be adapted based on the OCT-image.

At an another location of the anterior eye 50 illustrated in FIG. 8 a fluid conduit 65' connecting the anterior chamber 52 to the sclera 55 has already been established by treating the corresponding portion by a laser beam 34.

Figure 9:
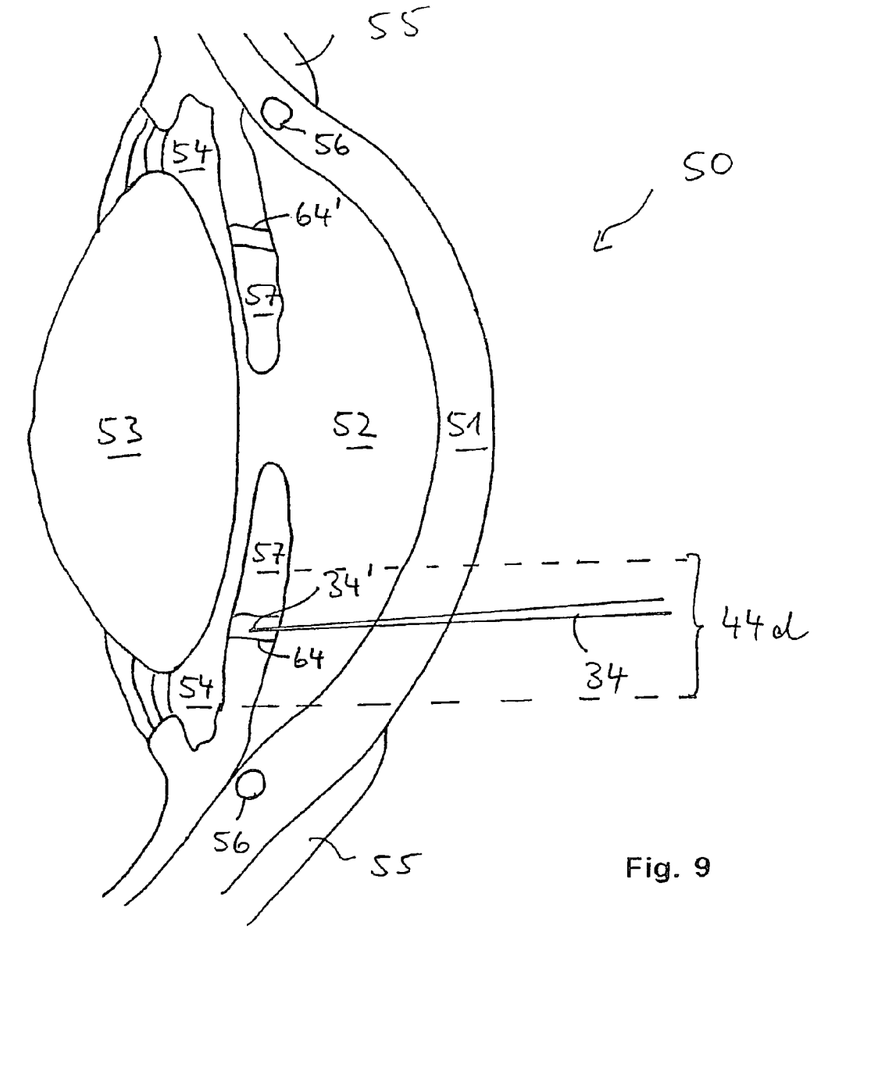
FIG. 9 schematically illustrates a method step of a method for treating glaucoma in an eye of a patient according to an exemplary embodiment of the present disclosure.

FIG. 9 illustrates another example of an embodiment according to the present invention for treating glaucoma in an eye of a patient. In this particular illustrated example it is intended to form a fluid conduit 64 through the iris from the anterior chamber 52 of the eye to the posterior chamber of the eye. To monitor a progress of a laser treatment by a laser beam 34 an OCT-image is acquired from a volume portion 44d. Inspection of the acquired OCT-image enables the surgeon to decide whether treatment by the laser beam 34 should continue and/or whether the positioning, the focusing, and the energy output of the laser beam 34 is appropriate for performing a successful treatment. In another part of the iris a fluid conduit 64' is already formed.

In all aforementioned examples of treating a particular anatomical structure within the eye this anatomical structure can be tracked such that it remains in the field of view of the system 1 even if it moves during treating, such as by breathing of the patient or by movements caused by the treating.

The exemplary embodiments set forth herein are intended to be illustrative and not limiting in any way. It will be appreciated that many alternatives, modifications and variations will be apparent to those skilled in the art. Accordingly, various changes may be made without departing from the spirit and scope of the present invention as set forth in the following claims.

What is claimed is:

1. A method for treating glaucoma in an eye of a patient, the method comprising:
    providing a combined system comprising a surgical microscope, an OCT apparatus, and a laser treatment apparatus;
    imaging a part of the eye onto a spatially resolving detector using the surgical microscope of the combined system;
    recording an image of the part of the eye detected by the spatially resolving detector;
    storing the recorded image in a storage device;
    processing the stored image using an image processing device, wherein processing the stored image comprises:
        identifying a distinguishable anatomical structure of an anterior portion of the eye in the recorded image; and
        predicting a volume portion of the anterior portion of the eye based on the identified anatomical structure;
    then acquiring a first OCT-image of the predicted volume portion of the anterior portion of the eye using the OCT apparatus of the combined system, wherein acquiring the first OCT-image comprises:
        selecting, based on the predicted volume, a scanning path extending within the predicted volume portion of the anterior portion of the eye;
        scanning an OCT measuring beam along the scanning path;
        recording OCT data corresponding to the scanning path; and
        generating the first OCT-image based on the recorded OCT data, wherein the first OCT-image is three-dimensional; and
    treating the volume portion using the laser treatment apparatus of the combined system to direct a laser beam to the volume portion to modify material in the predicted volume portion of the anterior portion of the eye based on the first OCT-image.

2. The method according to claim 1, further comprising:
    using the OCT apparatus for acquiring a second OCT-image of the volume portion of the eye; and
    further treating the volume portion by the laser beam based on at least one of the first and the second OCT-images.

3. The method according to claim 2, wherein the treating of the volume portion by directing the laser beam to the volume portion comprises adjusting at least one of
    a) an output energy of the laser beam,
    b) a positioning of the laser beam, and
    c) a spot size of the laser beam based on at least one of the first OCT-image, the second OCT-image, and a difference between the first and the second OCT-images.

4. The method according to claim 2, wherein the acquiring of at least one of the first or the second OCT-images comprises laterally scanning the OCT measuring beam across the volume portion according to the scanning path and detecting light intensities emanating from scanned parts of the volume portion, wherein a geometry of the scanning path is based on the recorded image.

5. The method according to claim 2, further comprising:
    locating a trabecular meshwork;
    modifying at least a part of the trabecular meshwork by the laser beam; and
    identifying in at least one of the first or the second OCT-images a Schlemm's canal, wherein the modifying the at least a part of the trabecular meshwork comprises preventing modifying Schlemm's canal.

6. The method according to claim 1, wherein the locating of the volume portion comprises locating a volume portion in a cornea extending from an anterior chamber to a sclera close to an anterior irido-corneal chamber angle opening and close to a trabecular meshwork and wherein the treating comprises directing the laser beam to the located volume portion to modify material of the located volume portion.

7. The method according to claim 6, further comprising analysing at least one of the first and the second OCT-images to determine whether material in the located volume portion in the cornea extending from the anterior chamber to the sclera has been modified providing a fluid conduit connecting the anterior chamber to the sclera through the cornea, wherein the treating is stopped when the fluid conduit is formed.

8. The method according to claim 1, wherein the locating of the volume portion comprises locating a trabecular meshwork and the treating comprises modifying at least a part of the trabecular meshwork by the laser beam.

9. The method according to claim 1, wherein the locating the volume portion comprises locating an iris and the treating comprises modifying the iris by the laser beam to provide a fluid conduit connecting an anterior chamber to a posterior chamber of the eye through the iris.

10. The method according to claim 1, wherein the locating of the volume portion comprises locating a ciliary body adjacent to a posterior chamber of the eye and the treating comprises modifying the ciliary body by the laser beam.

11. The method according to claim 1, wherein the predicted volume portion is located outside of the identified anatomical structure.

12. The method according to claim 11, wherein the identified anatomical structure comprises an iris of the eye and wherein the predicted volume portion includes at least one of a Schlemm's canal of the eye and a trabecular meshwork of the eye.

13. The method according to claim 1, wherein the predicted volume portion comprises an anatomical structure different from the distinguishable anatomical structure identified in the recorded image.

14. The method according to claim 13, wherein the distinguishable anatomical structure comprises an iris of the eye and wherein the predicted volume portion includes at least one of a Schlemm's canal of the eye and a trabecular meshwork of the eye.

15. The method according to claim 1, wherein the lateral scanning is performed using a scanning apparatus having a maximal scanning range, wherein the lateral scanning across the volume portion comprises less than 80% of the maximal scanning range.

16. The method according to claim 1, wherein the predicted volume portion is located outside of the identified anatomical structure.

17. The method according to claim 16, wherein the identified anatomical structure comprises an iris of the eye and wherein the predicted volume portion includes at least one of a Schlemm's canal of the eye and a trabecular meshwork of the eye.

18. A method for treating glaucoma in an eye of a patient, the method comprising:
   providing a combined system comprising a surgical microscope and an OCT apparatus;
   imaging a part of the eye onto a spatially resolving detector using the surgical microscope of the combined system;
   recording an image of the part of the eye detected by the spatially resolving detector;
   storing the recorded image in a storage device;
   processing the stored image, using an image processing device, wherein processing the stored image comprises:
      identifying a distinguishable anatomical structure of an anterior portion of the eye in the recorded image; and
      predicting a volume portion of the anterior portion of the eye based on the identified anatomical structure;
   then acquiring a first OCT-image of the predicted volume portion of the eye using the OCT apparatus of the combined system, wherein acquiring the first OCT-image comprises:
      selecting, based on the predicted volume, a scanning path extending within the predicted volume portion of the anterior portion of the eye;
      scanning an OCT measuring beam along the scanning path and recording OCT data corresponding to the scanning path;
      generating the first OCT-image based on the recorded OCT data, wherein the first OCT-image is three-dimensional; and
   treating the volume portion by inserting an implant at the volume portion based on the first OCT-image.

19. The method according to claim 18, further comprising:
   using the OCT apparatus for acquiring a second OCT-image of the volume portion of the eye; and
   further treating the volume portion based on at least one of the first and the second OCT-images.

20. The method according to claim 18, wherein the locating the volume portion comprises locating a Schlemm's canal and the treating comprises inserting a fibre into at least a part of the Schlemm's canal.

21. The method according to claim 20, further comprising analysing at least one of the first OCT-image, the second OCT-image, and the optical microscopic image to determine an amount of dilatation of the Schlemm's canal due to the inserted fibre.

22. The method according to claim 21, further comprising adjusting at least one of a positioning and a length of the fibre such that an amount of dilatation of the Schlemm's canal deviates less than a predetermined threshold from a predetermined amount of dilatation.

23. The method according to claim 18, wherein the locating of the volume portion comprises locating a Schlemm's canal and locating an anterior chamber and wherein the treating comprises inserting a tube shunt into a portion of the eye such that the tube shunt provides a fluid conduit from the anterior chamber to the Schlemm's canal.

24. The method according to claim 18, wherein the locating the volume portion comprises locating a sclera and locating an anterior chamber and wherein the treating comprises inserting a tube shunt into a portion of the eye such that the tube shunt provides a fluid conduit from the anterior chamber to the sclera.

25. The method according to claim 18, wherein the predicted volume portion comprises an anatomical structure different from the distinguishable anatomical structure identified in the recorded image.

26. The method according to claim 25, wherein the distinguishable anatomical structure comprises an iris of the eye and wherein the predicted volume portion includes at least one of a Schlemm's canal of the eye and a trabecular meshwork of the eye.

27. The method according to claim 18, wherein the lateral scanning is performed using a scanning apparatus having a maximal scanning range, wherein the lateral scanning across the volume portion comprises less than 80% of the maximal scanning range.

* * * * *